(12) United States Patent
Sahlén et al.

(10) Patent No.: US 10,287,621 B2
(45) Date of Patent: May 14, 2019

(54) TARGETED CHROMOSOME CONFORMATION CAPTURE

(71) Applicant: Pelin Sahlén, Uppsala (SE)

(72) Inventors: Pelin Sahlén, Uppsala (SE); Rickard Sandberg, Stockholm (SE)

(73) Assignee: PELIN SAHLÉN, Uppsala (SE)

( * ) Notice: Subject to any disclaimer, the term of this patent is extended or adjusted under 35 U.S.C. 154(b) by 490 days.

(21) Appl. No.: 14/783,685

(22) PCT Filed: Apr. 11, 2014

(86) PCT No.: PCT/SE2014/050451
§ 371 (c)(1),
(2) Date: Oct. 9, 2015

(87) PCT Pub. No.: WO2014/168575
PCT Pub. Date: Oct. 16, 2014

(65) Prior Publication Data
US 2016/0076081 A1 Mar. 17, 2016

(30) Foreign Application Priority Data

Apr. 11, 2013 (SE) .................................. 1300264
Jun. 13, 2013 (SE) .................................. 1350724

(51) Int. Cl.
*C12Q 1/68* (2018.01)
*C12Q 1/6806* (2018.01)

(52) U.S. Cl.
CPC ............. *C12Q 1/6806* (2013.01); *C12Q 1/68* (2013.01)

(58) Field of Classification Search
None
See application file for complete search history.

(56) References Cited

U.S. PATENT DOCUMENTS

| 9,434,985 B2 | 9/2016 | Dekker et al. |
| 2004/0023207 A1* | 2/2004 | Polansky ............... A61K 31/00 435/5 |
| 2013/0096009 A1* | 4/2013 | Dekker .................... C12Q 1/68 506/2 |

(Continued)

OTHER PUBLICATIONS

International Search Report for PCT/SE2014/050451 dated Jul. 22, 2014.

(Continued)

*Primary Examiner* — Samuel C Woolwine
(74) *Attorney, Agent, or Firm* — Stephen J. Weyer, Esq.; Stites & Harbison PLLC

(57) ABSTRACT

The invention relates to a method which enables the possibility to capture chromosome conformation as well as a kit containing components useful to be used the method, such as to detect promoter and enhancer relations. The method comprises the following steps: i) providing cross-linked genomic DNA, wherein the DNA comprises a first and a second set of regions, ii) fragmenting the cross-linked genome, thus creating a plurality of fragments with junctions, iii) adding a labelled junction marker such as biotin and ligating the fragments to the marker, iv) purifying the marked fragments, v) adding labelled capture probes and selectively purifying the hybridized fragments, and vi) analyzing the fragments captured by hybridization and identify the fragments.

11 Claims, 14 Drawing Sheets

(56) References Cited

U.S. PATENT DOCUMENTS

2013/0183672 A1 7/2013 De Laat et al.
2013/0203605 A1 8/2013 Shendure et al.

OTHER PUBLICATIONS

Van Berkum N L et al., "Hi-C: A Method to Study the Three-dimensional Architecture of Genomes", J. Vis. Exp.(2010). (39).

Mamanova L et al.,"Target-enrichment strategies for next generation sequencing", 2010, Nature Methods, 2010, vol. 7, pp. 111-118.

Naumova N et al., "Analysis of long-range chromatin interactions using Chromosome Conformation Capture", 2012, Methods, vol. 58, pp. 192-203.

Mertes F et al., "Targeted enrichment of genomic DNA regions for nest-generation sequencing", Briefings in Functional Genomics (2011) 10 (6): pp. 374-386.

Belton J-M et al., "Hi-C:A comprehensive technique to capture the conformation of genomes", 2012, Methods, vol. 58, pp. 268-276.

Extended European Search Report, Application. No. 14782776.0, Dated: Nov. 2, 2016, 10 pages.

Dostie, Josée, et al., "Chromosome Conformation Capture Carbon Copy (5c): a Massively Parallel Solution for Mapping Interactions Between Genomic Elements", Jun. 29, 2007, pp. 1299-1309, vol. 16, Cold Spring Harbor Laboratory Press, Genome Research.

Lieberman-Aiden, Erez, "Comprehensive Mapping of Long-Range Interactions Reveals Folding Principles of the Human Genome", Oct. 9, 2009, pp. 289-293, vol. 326, www.sciencemag.org.

Wang, Junbai, et al., "Genome-wide Analysis Uncovers High Frequency, Strong Differential Chromosomal Interactions and their Associated Epigenetic Patterns in E2-mediated Gene Regulation", 2013, pp. 1-13, vol. 14, No. 70, BMC Genomics, http://www.biomedcentral.com/1471-2164/14/70.

Maniatis, Tom, et al., "Regulation of Inducible and Tissue-Specific Gene Expression", Jun. 5, 1987, pp. 1237-1245, vol. 236, Science.

* cited by examiner

TARGETED CHROMOSOME CONFORMATION CAPTURE

FIELD OF INVENTION

The invention relates to a method which enables the possibility to capture chromosome conformation as well as a kit containing components useful to be used in the method, such as to detect promoter and enhancer relations.

BACKGROUND OF INVENTION

Chromosomes and genomes, are generally believed to be organized in three dimensions such that functionally related genomic elements, e.g. silencers and enhancers and their target genes, are directly interacting or are located far away from each other.

Genomes are believed to be complex and are composed of nucleic acids and proteins as well as some other biological components.

The activity of genes is tightly regulated to achieve biological functions at the right time and place. Each gene carries a region called promoter, which is a short DNA sequence responsible for interpreting the signals in the cellular environment to decide whether the gene should be activated or not. Specific proteins (transcription factors) bind to the promoter sequence to initiate assembly or disassembly of the protein machinery to either activate or inactivate its gene. Both secondary as well as the tertiary conformational structures of the genomes as well as the regulatory elements constitute the architecture that initiate and directs the events that occurs within a cell. Event that could give rise to different diseases or disorders, or just be normal activities within the cell.

The technology developed by Lieberman-Aiden et al., 2009 (Chromosome conformation capture methodology (Hi-C)) have been used to map long-range interactions and which probes the three dimensional architecture of whole genomes.

Van Berkum L et al., 2010, J. Vis. Exp. Vol 39, e11869doi: 10.3791/1869 discloses the conventional Hi-C technology, which could be coupled to other techniques. However, so far all the techniques have had some draw backs and been very time consuming as well as most techniques have a very low resolution.

The new invented technique give rise to a significantly higher mapping of promoters and enhancers compared to other techniques (see example 2 in the application).

However, there are some limitations with the Hi-C technology, including that there is a need to sequence very deep to be able to resolve regulatory interactions between promoter and enhancer elements and thus the Hi-C technology is time consuming as well as expensive and there is a need of developing new techniques that can solve those problems and enable the possibility to evaluate and detect direct intra- and inter-chromosomal interactions between remote regulatory elements, and utilize the information to diagnose specific medical and/or biological conditions.

SUMMARY OF THE INVENTION

The object of the present invention is to provide a new improved method that could be used together with for example the above-mentioned Hi-C technology to reveal more data in a fast and efficient way in relation to genomes and the regulation of the activities within a cell. For example, enhancers constitute a large fraction of the genome and are essential for the regulation of genes.

The invention relates to a method, which combines chromosome conformation capture with target-based sequencing to increase resolution (to ~600 bp) and sensitivity for regulatory interactions. Using this method, which here is named HiCap, 144,751 promoter-enhancer interactions involving 15,042 promoters and 101,856 enhancers in mouse embryonic stem cells was found, many of which are novel enhancers. Unlike previous genome-wide chromatin conformation capture methods, the data includes promoters of thousands of non-expressed genes. By the invented method it was also possible to detect a large number of promoter-promoter and enhancer-enhancer interactions, arranged in a way that suggests clusters of interaction partners that allow complex information processing between enhancers. The method has the resolution that previous chromatin conformation capture methods have been lacking, finally providing a way to map regulatory interactions at the single enhancer/promoter level.

By the use of the new invented method it is now possible to use the information revealed to diagnose specific medical and/or biological conditions. In the clinical genetics setting, importance of DNA variation in regulatory regions (enhancers) in complex disease onset and progression has been long neglected due to lack of a methodology to generate a reduced functional set. HiCap approach enables annotating noncodingregulatory partners of promoters at a single enhancer level. This will extend the hunt for disease causing variants to regulatory elements in addition to coding regions of genes, providing a means to study the role of non-coding variation in disease pathology. Additional genetic risk factors could be discovered that could have been missed otherwise. With better understanding of contribution of non-coding variation to disease progression, choice of therapy can be more precise. Moreover this will create a demand for novel clinical therapies to improve patient survival rates.

In a first aspect the invention relates to a method comprising: i) providing a cross-linked genomic DNA, wherein the DNA is conserved so that the DNA is intact, wherein the DNA comprises a first and a second set of regions ii) fragmenting the cross-linked genome creating a plurality of fragments with junctions, iii) adding a labelled junction marker and ligating the fragments with junctions and marker under conditions such that the marker is ligated to the junctions; iv) purifying the fragments containing a marker ligated at the junction; v) adding labelled capture probes and select for fragments that are hybridised to the marked capture probes and vi) analysing the fragments containing a marker ligated to the junction and those hybridise to the marked capture probe to determine the identity of the fragments.

By the invented method the information to be obtained from the genomic interactions and regulations within a cell have been increased and the work load decreased and thus it will for the first time be able to use such a technology in the diagnose of specific medical as well as biological conditions.

The invention enables to investigate interactions, such as promoter regulatory interactions in a cheaper and less data-intensive manner. In a second aspect the invention relates to a kit, comprising: i) a enzyme that will remove biotinylated nucleotides from unligated fragment ends ii) a set of enzymes to prepare sequencing libraries for high-throughput sequencing, comprising of an enzyme repairing DNA ends, an enzyme and sequencing adapters to ligate adapters to the fragments iii) streptavidin beads to select for biotinylated fragments iv) a sequence capture probe set to capture only fragments complementary to the regions of interests (such as promoters) v) chemicals necessary for performing sequence capture reaction using capture probe set.

The kit could be used in the method described above.

Further advantages and objects with the present invention will be described in more detail, inter alia with reference to the accompanying drawings.

DETAILED DESCRIPTION OF THE INVENTION

Definitions

Figure 1:
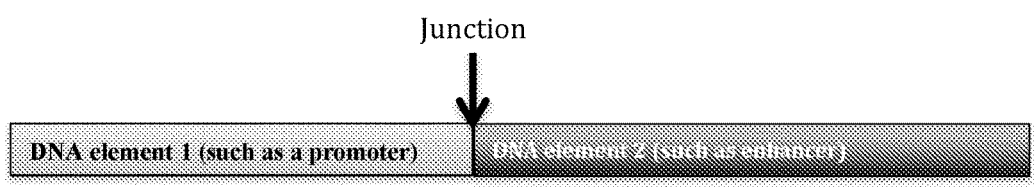
FIG. 1 shows a schematic presentation of chimeric sequences informing long-range genomic interaction such as between promoters and enhancers.

In the context of the present application and invention, the following definitions apply:

The term "junction" is intended to mean the site of ligation between two DNA fragments that do not reside next to each other in the genomic sequence but ligated together due to residing close to each other in the three-dimensional space in the nucleus (FIG. 1).

The term "junction marker" is intended to mean a compound that is capable of being incorporated within a nucleic acid and can provide a basis for selective purification in one or more steps. Examples of junction markers may include, a labelled nucleotide linker, a labelled and/or modified nucleotide, nick translation, primer linkers, or tagged linkers. Most of these being well-known for a person skilled in the art.

The term "labelled junction marker" is intended to mean a marker comprising any nucleic acid sequence comprising a label that may be incorporated (i.e., for example, ligated) into another nucleic acid sequence. For example, the label may serve to selectively purify the nucleic acid sequence (i.e., for example, by affinity chromatography). Such a label may include, but is not limited to, a biotin label or digoxigenin label.

The term "labelled capture probe" is intended to mean a short sequence of nucleotides comprising a label and is capable of hybridizing to another nucleotide sequence. For example, the label may serve to selectively purify specific nucleic acid sequences of interest. Such a label may include, but is not limited to, a biotin or digoxigenin label.

The term "conserved and intact" is intended to mean that the genomic DNA and the proteins are in the same configuration as in the cell and thus regulatory elements that are distantly located in the primary sequence of the genome from each other but are spatially close in the nuclear space in the conserved material which then also could be detected and identified by the invented technique, such as promoter and enhancer contact.

The term "first and second set of regions" are intended to mean nucleotides sequences that are located at different positions within the genome but that under specific conditions comes into contact with each other and by that being able to cooperate and direct events that occurs within the cell such as expression or silencing of specific genes.

The term "fragments" is intended to mean any nucleic acid sequence that is shorter than the sequence from which it is derived. Fragments can be of any size, ranging from several megabases and/or kilobases to only a few nucleotides long. Experimental conditions can determine an expected fragment size, including but not limited to, restriction enzyme digestion, sonication, acid incubation, base incubation, microfluidization etc.

The term "chromosome" is intended to mean naturally occurring nucleic acid sequence.

The term "analyzing" is intended to mean any process or method by which a collection of information is used to make a conclusion based upon sequence information. Examples include finding protein-coding sequences within a genome using sequence information obtained from experiments profiling transcription of genes.

The term "fragmenting" as used herein is intended to mean a method by which a nucleotide sequence is fragmented/separated into smaller unit fragments. Techniques to be used for fragmentation include enzymatic cleavage (i.e., for example, restriction enzymes acting upon nucleic acids or protease enzymes acting on proteins), base hydrolysis, acid hydrolysis, sonication or heat-induced thermal destabilization.

The term "marked capture probe" is intended to mean "is intended to mean a short sequence of nucleotides comprising a label and is capable of hybridizing to another nucleotide sequence. For example, the label may serve to selectively purify specific nucleic acid sequences of interest. Such a label may include, but is not limited to, a biotin or digoxigenin label.

The term "crosslink", "crosslinking" or "crosslink" is intended to mean stable chemical association between two compounds, such that they may be further processed as a unit. Such stability may be based upon covalent and/or non-covalent bonding. For example, nucleic acids and/or proteins may be crosslinked by chemical agents (i.e., for example, a fixative) such that they maintain their spatial relationships during routine laboratory procedures (i.e., for example, extracting, washing, centrifugation etc.) Many chemicals are capable of providing crosslinking, including but not limited to, formaldehyde, dimethyl adipimidate (DMA) or glutaraldehyde.

The term "ligated or ligation" is intended to mean linkage of two nucleic acid sequences usually comprising a phosphodiester bond. The linkage is normally facilitated by the presence of a catalytic enzyme (i.e., for example, a ligase) in the presence of co-factor reagents and an energy source (i.e., for example, adenosine triphosphate (ATP)).

The term "open reading frame" is intended to mean any nucleic acid sequence encoding a protein.

The term "regulatory element" is intended to mean a nucleic acid sequence that affects the expression of another genomic sequence. Examples are enhancers, repressors, insulators and locus control regions.

The term "hybridise or hybridisation" is intended to mean the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

The terms "restriction endonucleases" and "restriction enzymes" is intended to mean enzymes, which cut double-stranded DNA at or near a specific nucleotide sequence. DNA molecules are said to have "5' ends" and "3' ends" because mononucleotides are reacted to make oligonucleotides in a manner such that the 5' phosphate of one mononucleotide pentose ring is attached to the 3' oxygen of its neighbour in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located downstream of the coding region. Transcription termination and polyadenylation signals are located 3' end of the coding region.

The term "regulatory element" is intended to mean a genetic element, which controls some aspect of the expression of nucleic acid sequences. For example, a promoter is a regulatory element, which facilitates the initiation of transcription of an operably linked coding region. Other regulatory elements are splicing signals, polyadenylation signals, termination signals, etc. Transcriptional control signals in eukaryotes comprise "promoter" and "enhancer" elements. Promoters and enhancers consist of short arrays of DNA sequences that interact specifically with cellular proteins involved in transcription (Maniatis, T. et al., Science 236:1237 (1987)). Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest.

The term "labelled" is intended to mean compositions detectable by spectroscopic, photochemical, biochemical, immunochemical, electrical, optical or chemical means. Such labels include biotin for staining with labelled streptavidin conjugate or Cy3-flourophore labelling for fluorescent detection in microarrays.

The Method

The present invention relates to the interactions between genetic elements, which occur within the living cell. In a living cell, the activity of genes is tightly regulated to achieve biological functions at the right time and place. Each gene carries a region called promoter, which is a short DNA sequence responsible for interpreting the signals in the cellular environment to decide whether the gene should be activated or not. Specific proteins (transcription factors) bind to the promoter sequence to initiate assembly or disassembly of the protein machinery to either activate or inactivate its gene. Often there are DNA regions located distally in the genome fold onto the promoter sequences.

The three-dimensional conformation of chromosomes may be involved in compartmentalizing the nucleus and bringing widely separated functional elements into close spatial proximity. Understanding how chromosomes fold can provide insight into the complex relationships between chromatin structure, gene activity, and the functional state of the cell. Yet beyond the scale of nucleosomes, currently little is known about chromatin organization. Because deoxyribonucleic acid (DNA) is a linear molecule, the genome is often thought of as linear. However, chromosomes are not rigid, and so the spatial distance between two genomic loci need not correspond to their distance along the genome. Regions separated by many megabases can be immediately adjacent in 3-dimensional space. From the standpoint of regulation, understanding long-range interactions between genomic loci may be useful. For example, gene enhancers, silencers, and insulator elements might possibly function across vast genomic distances.

These distal DNA sequences are called enhancers and can also bind to specific proteins. The interactions between enhancer-bound and promoter-bound proteins contribute to the decision whether the gene will be activated or not. This process is called distal regulation of genes. Promoters of the genes are always found proximal to the genes, however distal regulatory regions can be far away in the primary sequence of the genome and it is not possible to know which distal regulatory elements fold and act on to which promoter from the primary DNA sequence itself. By the proposed method/invention it is now possible to know which regulatory elements regulate which promoter.

Figure 2:
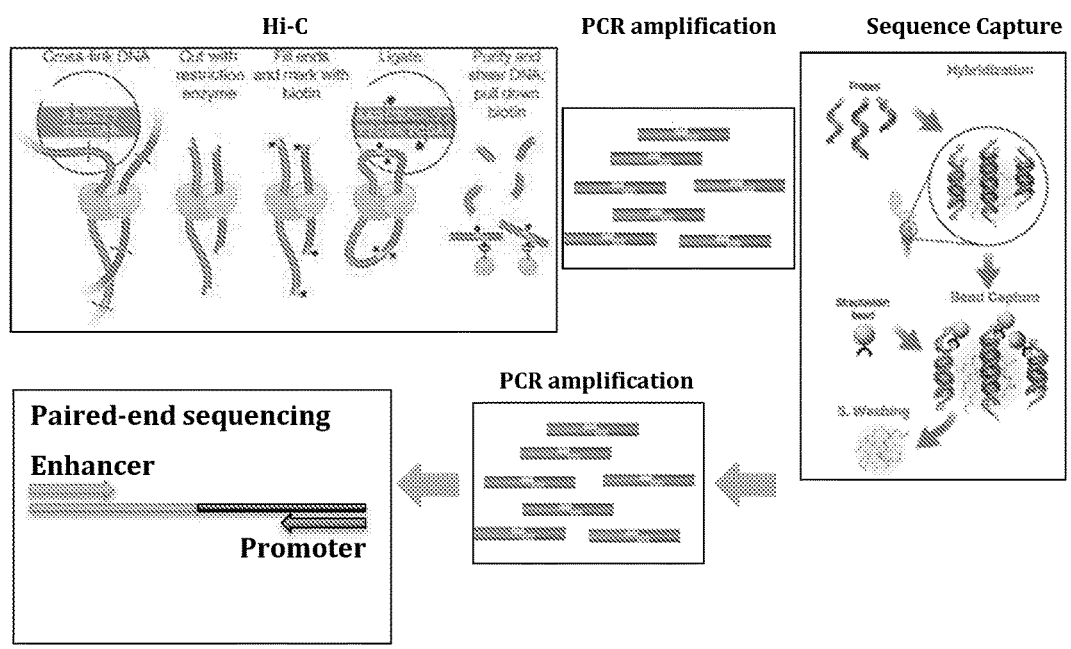
FIG. 2 shows an overview of HiCap methodology. A standard Hi-C protocol is applied with minor modification (the first subfigure is adopted from Lieberman-Aiden et al, 2009). A sequencing library is prepared by ligating sequencing adapters to the fragments (not shown here) and the fragments are amplified by PCR. Original biotinylated materials are removed (not shown here). Then these fragments are hybridized to sequence capture probes according to manufacturer's instructions (the third subfigure is adopted from Roche Nimblegen, Inc.). The uncaptured material is washed away and captured material is amplified. The amplified captured material is then sequenced in paired-end format.

Here is one example of a step-by-step description of HiCap methodology in the present invention (FIG. 2).

Figure 3:
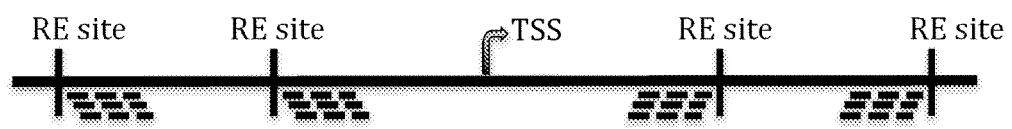
FIG. 3 shows a schematic representation of sequence capture probes per promoter. Four closest restriction enzyme sites (RE site) to the transcription start site (TSS) are chosen as target regions for probes. Each probe is around 90 bases long and they tile around 150-300 bases region, each around 5 bases away from each.

1. Sequence probes targeting promoters of relevant organism are designed around the restriction enzyme sites closest to transcription start site (FIG. 3). If the sequence around the closest restriction enzyme is not suitable for probe design due to high GC-content and presence of repeat elements, probes are designed for the next closest restriction enzyme. Probes should be designed so that they are sufficiently close to the promoter. Probes are designed for at least two restriction enzymes on each side of promoter (in total at least 4 restriction enzyme sites) to increase the probability of capturing promoter interactions. Additionally, probes are designed for around 400-1000 regions that are not close to any annotated promoter or regulatory element. These will constitute as negative control regions to determine background interaction levels.

2. A standard FIX protocol is applied to the cell line of interest. It is important to use a frequent restriction enzyme such as DpnII to reach better sequence resolution per regulatory element.

3. Original biotinylated materials are removed by binding the PCR-amplified material to streptavidin-coated beads and supernatant is preserved.

4. Supernatant is hybridized to custom designed sequence capture probes according to manufacturer's instructions.

5. Hybridized capture probes are washed according to manufacturer's instructions and the material is PCR-amplified and ready for sequencing.

6. The captured and PCR-amplified material is sequenced using Illumina HiSeq platform.

7. The read pairs are aligned to the appropriate genome.

8. Background interaction frequencies are calculated using read pairs that maps to target probes targeting non-regulatory regions.

9. Read pairs for which only one read of the pair mapping to a promoter region are selected and the genome coordinate of the other pair is kept as a putative interactor.

10. For each putative interactor, supporting number of pairs are counted and those that are significantly above background levels are assigned as putative enhancers of promoters they were linked to or as promoter-promoter interactions.

The invention relates in one aspect to a method comprising: i) providing a cross-linked genomic DNA, wherein the DNA is conserved so that the DNA is intact, wherein the DNA comprises a first and a second set of regions ii) fragmenting the cross-linked genome creating a plurality of fragments with junctions, iii) adding a labelled junction marker and ligating the fragments with junctions and marker under conditions such that the marker is ligated to the junctions; iv) purifying the fragments containing a marker ligated at the junction; v) adding labelled capture probes and selectively purify fragments that are hybridised to the marked capture probes and vi) analysing the fragments containing a marker ligated to the junction and which hybridise to the marked capture probe to determine the identity of the fragments.

The genomic DNA may be cross-linked/immobilised by fixation such as by formaldehyde and by doing that the DNA is conserved and intact. This step ensures that all the genomic DNA and proteins bound to it are covalently bound to each other so that the conformation of the genomic DNA stays intact during the rest of the method. The DNA is then fragmented which could be done by one or more restriction enzyme that leaves a number of bases unpaired at the site of digest creating a mix of fragments including a first and a second set of fragments being close to each other and interacting with each other. The DNA comprises sticky ends after the treatment with the restriction enzyme. Examples of restriction enzymes include HindIII, DpnII and BglII. The treatment of the DNA with the restriction enzyme may be performed for a number of hours up to over night depending on which enzyme is used.

The fragments, which bases are filled with a labelled junction marker, such as biotin labelled nucleotides. The DNA is then heat treated to deactivate the enzymes present within the sample.

Then the material is diluted and ligated so that the free DNA ends can be ligated to each other, such that the first and second of regions are ligated to each other. This is the step where the folding of the genome is captured: since the three-dimensional structure of the genome is preserved by crosslinking, regions that were close to each other (i.e. interacting) at the time of crosslinking can be ligated to each other even though they actually are far away in the primary sequence of DNA. Then the crosslinking is reversed and DNA is extracted. The material is now composed of DNA that contains sequences that were near each other in the three-dimensional space (FIG. 2). These chimeric sequences are called junction sequences and the site at which two distal sequences are adjacent is called junction (FIG. 2). First unligated biotinylated fragments are removed using T4 DNA polymerase. Then the DNA is fragmented by sonication, and biotinylated fragments are pulled down using streptavidin beads. This step ensures that only fragments that contain a junction will be investigated in the later steps. Those first steps are well known and described in van Berkum, N. L. et al., *J. Vis. Exp.* volume 39, (2010). (Hi-C technology).

Currently in the field, the resulting junction fragments are sequenced using next-generation sequencing technologies to unravel the genomic interactions. Interactions occurring between promoters and their regulatory elements (enhancers) are called regulatory interactions. However, Hi-C methodology captures any pair of genomic region that was close to each other at the time of crosslinking as an interaction. Many of such pairs represent regions in spatial proximity due to the structure of the genome. These events are called as structural interactions. Since many cells share similar genomic structure, structural interactions are more abundant than regulatory interactions, which are often tightly regulated and may be present only in a small number of cells at the time of crosslinking. Therefore, when one sequences a Hi-C experiment, structural interactions are resolved with better resolution than regulatory interactions. Even though Hi-C provides great insights for the three-dimensional structure of the genome, chromatin domains etc., one needs to sequence very deep to be able to resolve regulatory interactions occurring between promoters and their regulatory sequences (enhancers).

In one embodiment the invention relates to a method, which can be used select for/find junction sequences that for example inform on enhancer/promoter interactions. Today, junction sequences in Hi-C containing interactions with promoters not really representing distal regulation/enhancers will be sequenced That particular embodiment is used to select for only sequences of interest using specifically designed short DNA sequences called capture probes, which are labelled and then named labelled capture probes. Capture probes may be designed against promoter sequences since their sequence is known. These short sequences called capture probes will then be labelled such as being biotinylated. For example the first set of regions are promoter regions and the second set of regions comprises a regulatory sequences, such as enhancers, silencers, insulators, being located close or distantly from each other in the DNA or on the same or different chromosomes and in another example the second set of regions comprises enhancer sequences.

The labelled capture probes hybridize to their complementary sequences and are then pulled down by for example streptavidin-coated magnetic beads. Here in our method capture probes are designed for promoter sequences, and then the Hi-C material are hybridized to those probes to select only interactions of promoters. The captured sequence will contain the promoter sequence but also the sequence that it was proximal in space at the time of crosslinking. The captured material is then sequenced, only sequencing interactions of regions targeted by capture probes. This method enables to resolve promoter interactions with distal regulatory regions with less sequencing.

First the sequence capture probes are designed for promoter regions. To this end, a suitable restriction enzyme is selected to give an appropriate resolution of the regulatory regions. The enzyme should give a median fragment size between 500-1000 bp. HiCap has been applied to mouse embryonic stem cells (mESC) to map developmental enhancers at high resolution. A sequence-capture probe set (Roche Nimblegen Inc) consisting of 53,735 sequence-capture probes targeting 31,000 mouse promoters and 400 regions that are at least 100 kb away from promoters to serve as negative controls. Sequence capture is then performed on Hi-C material from mouse embryonic stem cells using these probes and sequenced on the Illumina HiSeq platform. One study yielded 144,751 promoter-anchored interactions involving 19,000 promoters and an additional 46,873 promoter-promoter interactions. In total, 101,856 putative enhancers (PE) could be mapped with an average of 609 bp resolution.

So far, ChIA-PET has been the best medium/high-throughput method available for studying regulatory elements (Li. G, et. al, Cell, 2012). Comparing HiCap to ChIA-PET (on K562 cells, RNA polymerase II pull-down), at similar sequencing depths, we found 3.3 times more enhancers at a 6 times higher resolution (Table 1). By comparing the overlap with ChIP-seq peaks, we also found that HiCap had higher specificity for enhancers (on average a 15-fold enrichment for overlap with ChIP-seq peaks).

TABLE 1

Comparison of ChIA-PET to HiCap methodology.

| Method | Total read pairs used | Number of enhancers | Average enhancer length (bp) |
|---|---|---|---|
| ChIA-PET (K562 Pol2) | 30M | 33,682 | 3,789 |
| HiCap (mES) | 37M | 109,864 | 609 |

To investigate the regulatory potential of enhancers found by HiCap, a comparison was done with public data. To this end, 12 ChIP-Seq and a DNase hypersensitivity dataset was downloaded (ChIP-Seq datasets for H3K4me1, H3K27Ac, H3K9Ac, CTCF, Cohesin, Mediator complex, a collection of mESC-specific transcription factors, p300, ENCODE mESC-specific enhancer set, low-methylated regions, and mESC-specific DNase hypersensitivity sites, available via mouse ENCODE project, *PLoS Biol*, e1001046, 2011)). 67% of intra-chromosomal HiCap enhancers overlapped with at least one ChIP-seq peak was found.

RNA-Seq was performed to generate gene expression profiles of mESCs. Of the 20,558 annotated promoters of protein-coding genes, we detected at least one distal interaction for 91% of the highly expressed genes (428 of 469), 85% (10,423 of 12,210) of genes expressed in medium levels and 69% (4,043 of 7,879) of the lowly expressed genes. With the help of expression data it was also possible to test whether regulation by the same enhancer results in similar expression levels. While the expression of genes connected to the same enhancers had a coefficient of variation of 0.66 on average, for closely related samples (cell lines for trophectoderm, primitive endoderm and epiblast) they were higher, at 0.68 (P=2*10$^{-20}$, Wilcoxon rank sum test), 0.67 (P=0.005) and 0.67 (P=0.01) respectively. Thus, there was a co-regulation using the regulatory interactions that was detected, while controlling for the effect of similarly expressed genes residing close to one another.

In another aspect the invention relates to a kit, comprising: i) a enzyme that will remove biotinylated nucleotides from unligated fragment ends ii) a set of enzymes to prepare sequencing libraries for high-throughput sequencing, comprising of an enzyme repairing DNA ends, an enzyme and sequencing adapters to ligate adapters to the fragments iii) streptavidin beads to select for biotinylated fragments iv) a sequence capture probe set to capture only fragments complementary to the regions of interests (such as promoters) v) chemicals necessary for performing sequence capture reaction using capture probe set.

Following examples are intended to illustrate, but not to limit, the invention in any manner, shape, or form, either explicitly or implicitly.

EXAMPLES

Example 1

Sequence probes targeting promoters of relevant organism were designed around the restriction enzyme sites closest to transcription start sites (FIG. 3). This was repeated for all promoter regions, then, these target regions were sent to the company (Roche Nimblegen, Inc.) for design and manufacturing of the probes. Additionally, probes were also designed for around 500-1000 regions that are not close to any annotated promoter or regulatory element to calculate the frequency of randomly occurring interactions due to proximity rather than function (background interaction frequency).

Note that, there is no need to know any enhancer sequence in advance since they will be captured together with promoter sequences by capture probes.

The probes can be designed not only against promoters but also for any set of region of interest, such as particular genomic regions, or disease-associated not-annotated genomic regions.

These will constitute as negative control regions to determine background levels. A standard HiC protocol was applied to the cell line of interest. In this experiment, mouse embryonic stem cells were used. It is imperative to use a frequent restriction enzyme to reach better sequence resolution per regulatory element and we used DpnII, it fragments human genomic DNA on average every 800 bases (±bases).

Original biotinylated materials were removed by binding the PCR-amplified material to streptavidin-coated beads and supernatant was preserved. This was a necessary step since original biotinylated material represents the whole genome, they should not be sequenced. They will be captured during sequence capture step together with biotinylated sequence capture probes. Therefore we remove them and only hybridize the amplified material from the original biotinylated material to the sequence probes. The hybridization is performed according to manufacturer's instructions (Roche Nimblegen, Inc.).

Hybridized capture probes were washed according to manufacturer's instructions (Roche Nimblegen, Inc.) and the material is PCR-amplified and ready for sequencing. The captured and PCR-amplified material is sequenced using Illumina HiSeq platform (Illumina Inc).

The read pairs were aligned to the mouse genome. Read pairs which span less than 1 kilobase distance to each other were discarded since they do not inform about distal interactions. Then background interaction frequencies were calculated using read pairs that maps to target probes targeting non-regulatory regions.

Read pairs of which only one read of the pair mapping to a promoter region were selected and the genome coordinate of the other pair was kept as a putative interactor.

For each putative interactor, supporting number of pairs are counted and those that were significantly above background levels are assigned as putative enhancers of promoters they were linked to or as promoter-promoter interactions.

Example 2

Experimental Set Up

Figure 4:
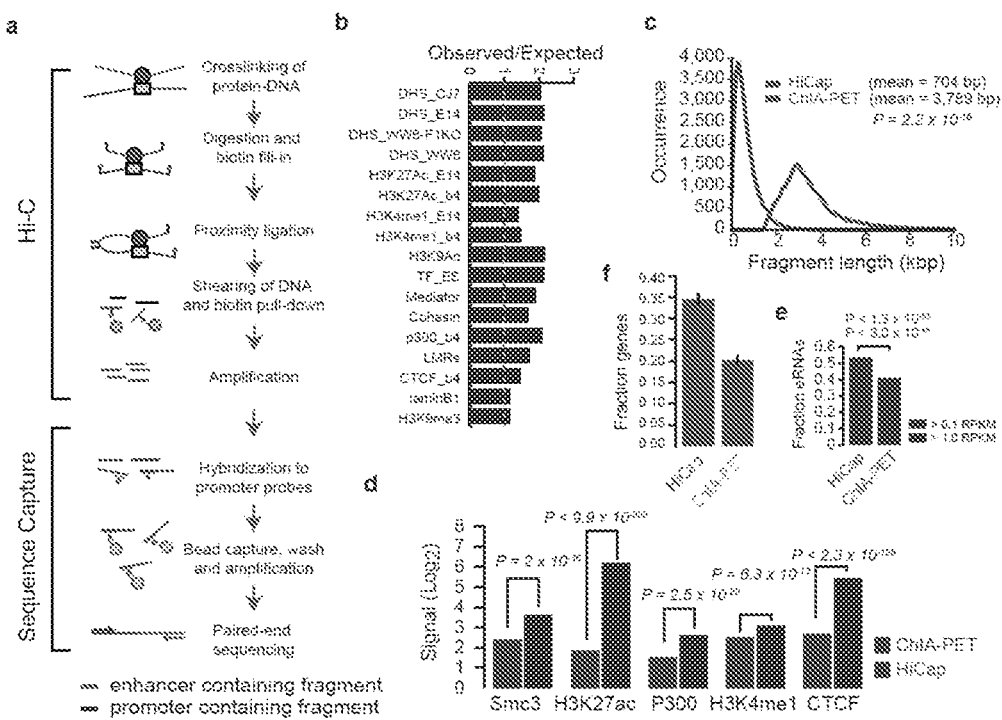
FIG. 4 shows the invented technology.
Figure 7:
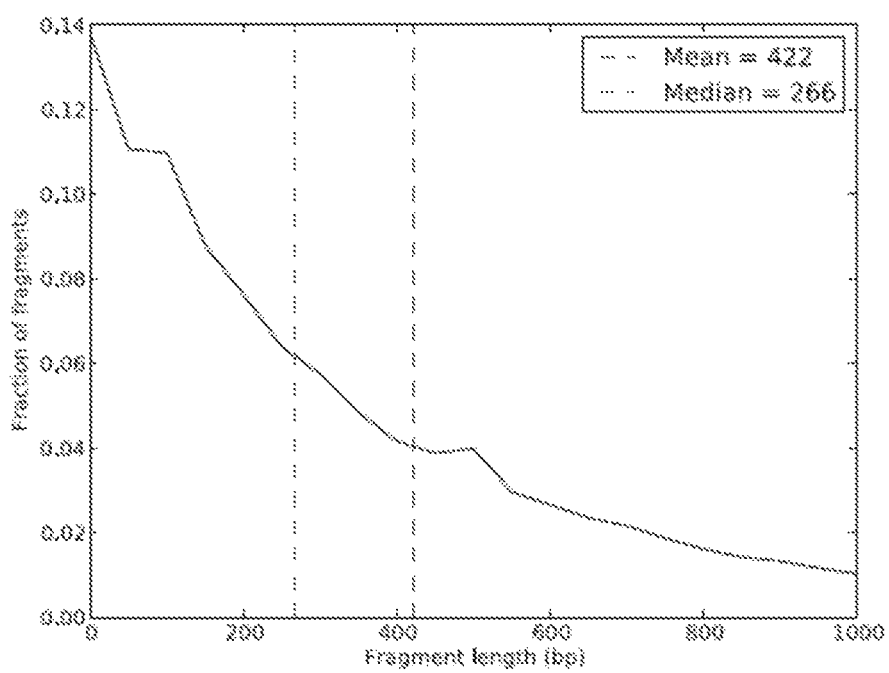
FIG. 7 shows the theoretical mean fragment size for the 4-cutter (MboI).
Figure 8:
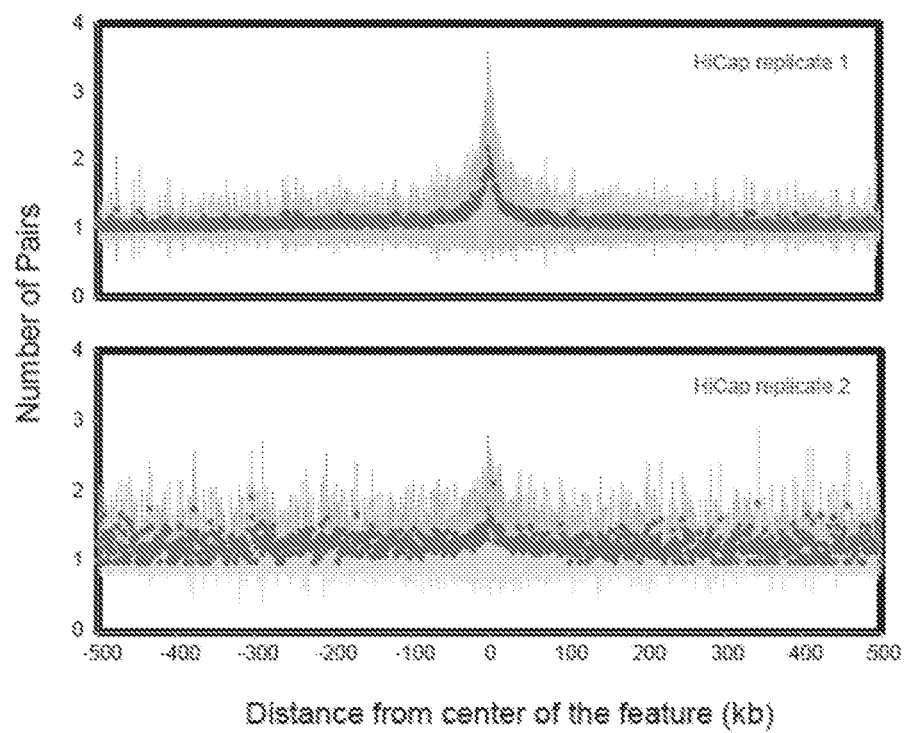
FIG. 8 shows the interactions anchored on negative control regions (the targeted intergenic and exonic regions) were used to estimate the background as a function of distance between read pairs.
Figure 9:
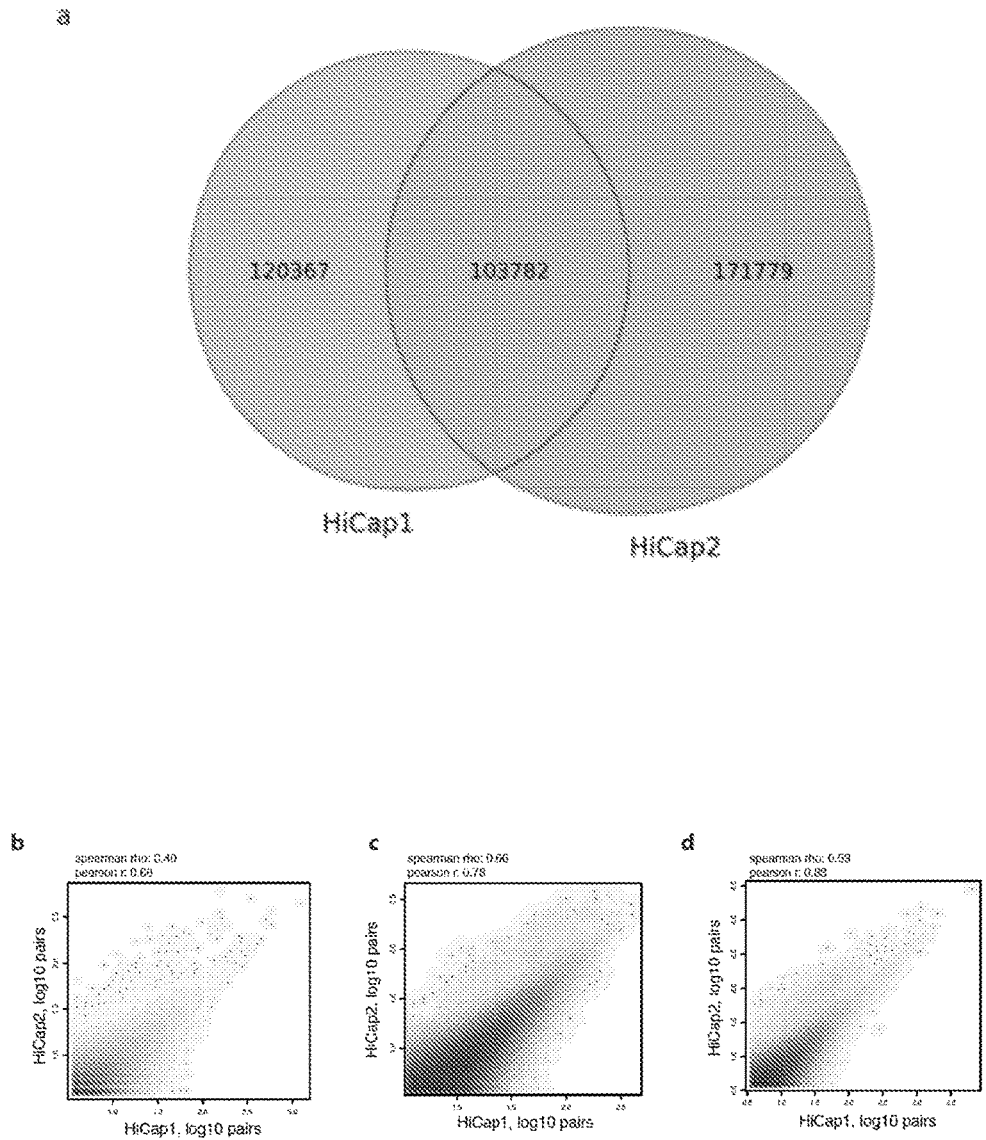
FIG. 9 shows filtered interactions based on pair support in replicates.

In order to generate a high-resolution map of long-range regulatory interactions, HiCap was developed that extends Hi-C through an additional sequence-capture of promoter containing fragments to simultaneously map long-range interactions for both transcribed and non-transcribed genes (FIG. 4a). To improve resolution, the initial Hi-C using a 4-cutter (MboI) with a theoretical mean fragment size of only 422 bp was performed (FIG. 7). Capture probes were designed for restriction fragments containing mouse promoters (31,127 promoters in 16,696 unique genes) and additional control regions in intergenic regions and exons (n=184). Two biological replicate HiCap libraries from mouse embryonic stem cells (mESC) were generated and sequenced the libraries from both ends (2×100 bp) to a depth of 200-300 M read pairs. Reads were mapped independently and read pairs were discarded if they mapped within 1 kb of each other (to remove self-ligated fragments). The estimated efficiency of the restriction enzyme was 71%. The interactions anchored on negative control regions (the targeted intergenic and exonic regions) were used to estimate the background as a function of distance between read pairs (FIG. 8). Next, we called promoter-anchored interactions, requiring interactions to be supported by significantly more pairs (2 standard deviations above the mean) than background in both biological replicates. We subsequently filtered interactions based on pair support in both replicates (FIG. 9) to obtain 151,740 interactions (min 4 pairs) and 13,527 high-confidence interactions (min 14 pairs), involving 17,255 genes (7,808 for high-confidence interactions). These interactions included both interactions from promoters to distal regions (68% of all interactions), and interactions between two promoter regions. Intrachromosomal interactions dominated both promoter-distal (94%) and promoter-promoter (99%) interactions.

Figure 10:
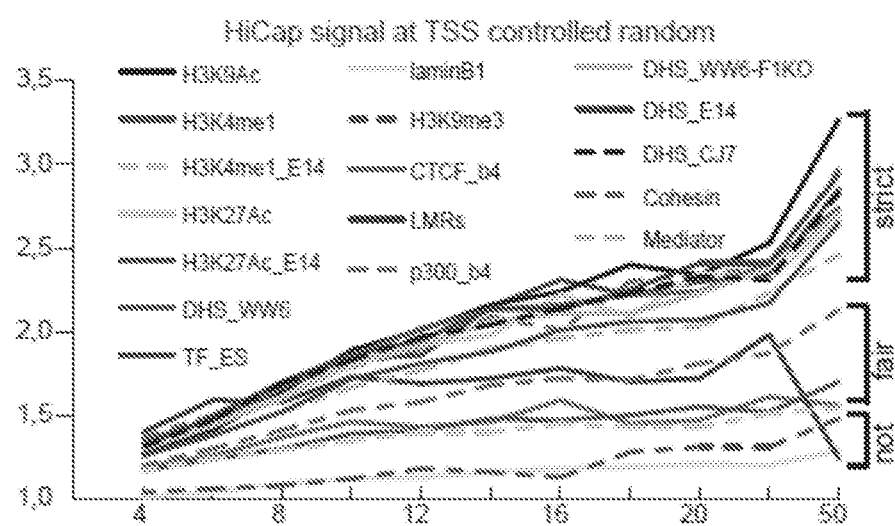
FIG. 10 shows high-confidence HiCap interaction results.
Figure 11:
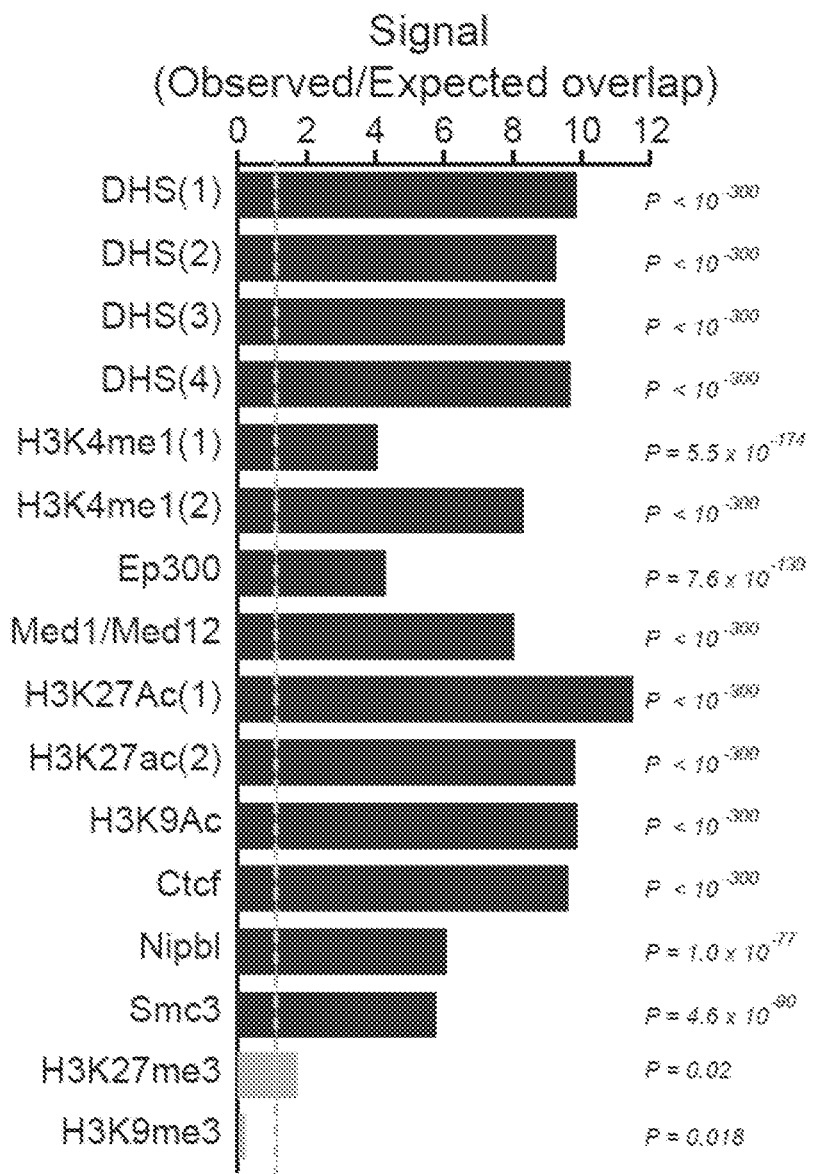
FIG. 11 shows computing expected fractions using a fully random background model yielded higher overlaps with enhancer marks but also other chromatin marks.

In order to validate our HiCap interactions from promoters to distal regions, we investigated to what extent they were enriched for known mESC enhancers. We assessed the enrichment as the ratio of observed to expected overlap. To incorporate the non-random locations of promoters and enhancers into our background model, we computed expected fractions through randomly sampling fragments from annotated promoters using the observed distance distributions of HiCap interactions. We found that high-confidence HiCap interactions were significantly ($P=3.4\times10^{-34}$ to $P<10^{-300}$ for all enhancer data, Chi-square test) enriched for previously mapped enhancers (FIG. 4b and FIG. 10), but not for transcriptionally silent chromatin with H3K27me3 marks ($P=0.6$, Chi-square test). Moreover, heterochromatin regions marked with H3K9me3 were depleted among HiCap interactions (FIG. 4b). Computing expected fractions using a fully random background model yielded higher overlaps with enhancer marks but also other chromatin marks (FIG. 11). These results demonstrated that our promoter-anchored interactions were highly enriched for known enhancers.

Figure 5:
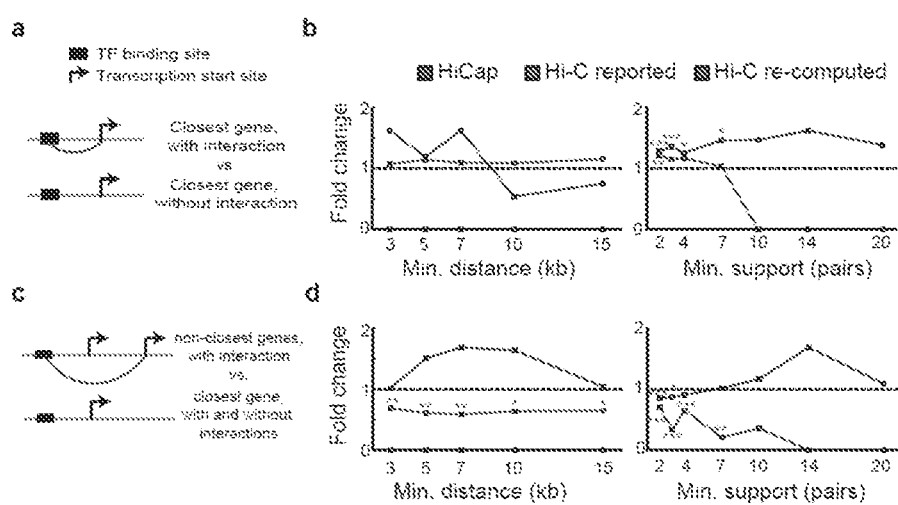
FIG. 5 shows genome-wide binding location of 15 different transcription factors and analysis using the invented technology.
Figure 12:
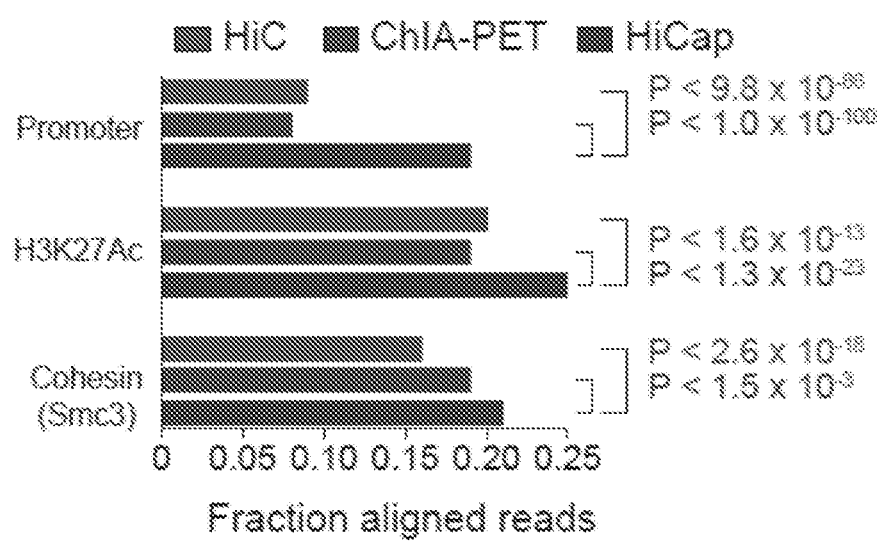
FIG. 12 shows comparison of HiCap with other techniques.
Figure 13:
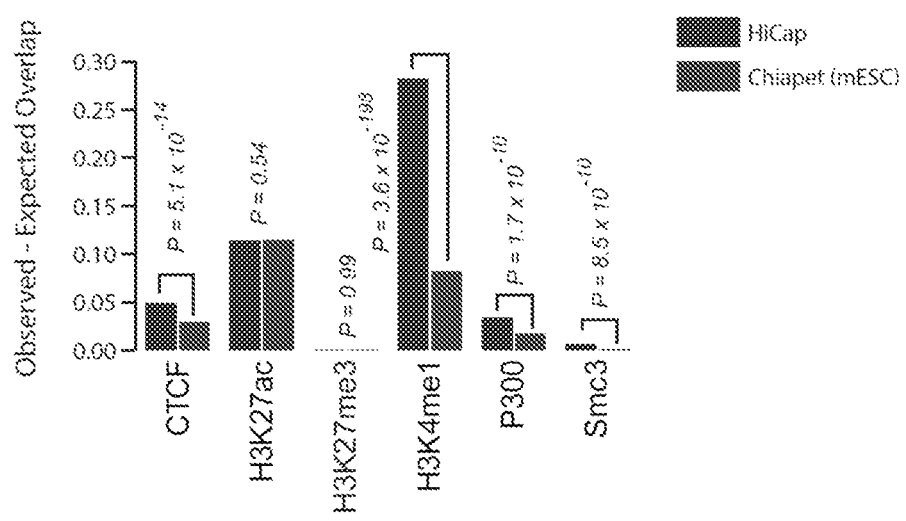
FIG. 13 shows comparison between different techniques.

To determine how HiCap compared to previous methods, we next compared our interactions to published Hi-C data in mESC and ChIA-PET data generated with RNA polymerase II (RNA pol II) immunoprecipitation in K562 cells. Comparing the raw mapping frequencies to promoters and enhancers demonstrated that HiCap had significantly higher percent reads aligning to both known promoters ($P<10^{-86}$, Chi-square test) and enhancers ($P<10^{-13}$ for H3K27Ac; $P<10^{-3}$ for Cohesin, Chi-square test) than both Hi-C and ChIA-PET (FIG. 12). The ChIA-PET data had a mean fragment length of 3,789 nts but HiCap interactions had significantly ($P=2.2\times10^{-16}$, Chi-square test) shorter fragment sizes (mean=704 nts) (FIG. 4c), an adequate resolution to map individual enhancers. Moreover, HiCap interactions were more significantly ($P<1.4\times10^{-20}$, Fisher's exact test) enriched for published enhancers than ChIA-PET interactions, when comparing their overlap to several enhancer location data in K562 cells (FIG. 4d), and in comparisons using recent published ChIA-PET interactions from mESC (FIG. 13). We next re-analyzed RNA-seq data to investigate enhancer RNA (eRNA) expression, and HiCap interactions had significantly ($P=3\times10^{-46}$, Chi-square test) more eRNA expression than ChIA-PET interactions (FIG. 4e), providing separate support for the higher purity in bona fide interactions captured with HiCap. Another potential strength with HiCap is the potential to map interactions for both actively transcribed and silent genes, whereas ChIA-PET interactions capture only genes bound by the targeted protein (often RNA pol II). We found that 34% of non-transcribed genes (<0.1 RPKM) had a mapped interaction, compared to only 18% in ChIA-PET (FIG. 4f). We re-analyzed genome-wide binding locations of 15 different transcription factors (TFs) in mESC together with genome-wide differential expression analyses after TF overexpression to determine whether genes with HiCap interactions linking them to mapped enhancers were more often found upregulated. We first focused on the closest genes of mapped TFs (FIG. 5a) and found that genes with HiCap interaction support were more often upregulated than those without HiCap interaction support (FIG. 5b). The higher enrichment was significant ($P<0.001$, Fisher's exact test) for HiCap interactions at several read thresholds (FIG. 5b), as well as Hi-C interactions (only at ≥2 reads) (FIG. 5b). To investigate the functional relevance of interactions between enhancers and non-closest genes, we evaluated their enrichment for upregulated genes. High-confidence HiCap interactions to more distant genes had similar and sometimes even significantly higher enrichment for upregulated genes than the set of closest genes (FIG. 5c-d). In particular, we identified significantly better enrichments than the closest set of genes for experiments with Tcfcp2l1 and Myc (FIG. 13), whereas interactions to known binding sites of other factors such as Klf4 had similar enrichments as the closest gene sets. Published Hi-C in mESC however was consistently worse than the closest gene set. This functional validation gives confidence that HiCap interactions can predict gene expression changes after TF perturbations.

Figure 6:
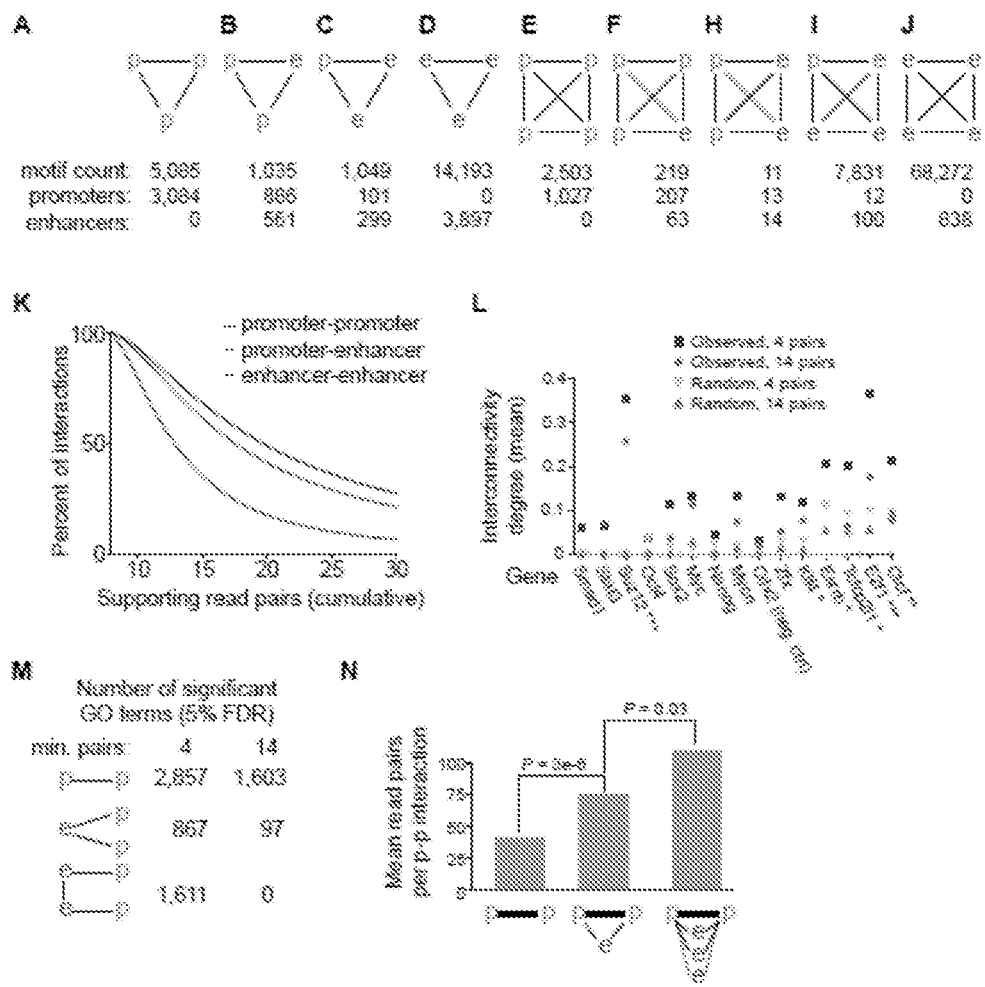
FIG. 6 shows the investigation of whether global HiCap interactions could inform on general organisation of regulatory interactions.

Gene regulation in the nucleus has a spatial component and we investigated whether global HiCap interactions could inform on general organization of regulatory interactions. We noted an apparent enrichment for interconnected clusters (cliques) of only promoters (FIG. 6a), only enhancers (FIG. 6j) compared to motifs involving both enhancers and promoters (FIG. 6b-i). Interactions involving two promoters were likely over-represented due to sequence capture, but surprisingly we detected high read support for interactions involving two enhancers (despite sequence capture). Moreover, read support for interactions involving two enhancers were higher than interactions between a promoter and an enhancer (FIG. 6k), providing additional support for enhancer-enhancer interactions and indicating that they are prevalent, even more prevalent than promoter-promoter interactions. Further analyses of the enhancer-enhancer interactions revealed that they were more often bound by the same TF factor than what would be expected by chance, with significant enrichments for E2f1 and a trend towards enrichments for other factors (FIG. 6l). Interestingly, genes connected through promoter interactions or mutual promoter-enhancer interactions were more often annotated to belong to the same Gene Ontology categories (FIG. 6m) supporting the previous finding that such interactions could be involved in transcriptional coordination. Finally, we observed that two genes with interacting promoters had more pair support if they were additionally interacting with one or two or more enhancers (FIG. 6n).

Methods

Mouse ES Cells.

Mouse embryonic stem cells (line R1) were obtained from Janet Rossant's lab (Toronto, Canada). Cells were maintained on 0.1% gelatin-coated dishes in Dulbecco modified Eagle medium (DMEM) supplemented with 10% fetal calf serum (FCS), 0.1 mM non-essential amino acids, 0.3 mg/ml L-glutamine, 1 mM pyruvate (Invitrogen), 1000 U/ml murine LIF (Chemicon International ESGRO), and were kept in a 5% CO2 atmosphere at 37° C. The medium of undifferentiated cells was changed daily.

HiCap.

Hi-C was performed on mouse embryonic stem cells as previously described[9], except for the following modifications below. We generated replicate experiments from 20 million mouse embryonic stem cells (mESC) that were cross-linked with 1% formaldehyde for 10 minutes. Cells were lysed and nuclei were isolated. Isolated nuclei were digested with 4-cutter FastDigest MboI (Thermo Scientific, 1 μl/μg DNA) for 4 hours at 37° C. The ends of digested material were filled with biotinylated dATP, dGTP, dCTP and dTTP using Klenow fragment (Fermentas, 0.1 U per 1 μg DNA). Klenow was deactivated using 0.01 M EDTA at incubating 75 C for 15 minutes. Then the material was diluted to 3.5 ng/μl and ligated using T4 DNA Ligase (Promega). The crosslinking was reversed by adding Proteinase K and incubating overnight at 65 C. The proteins were removed and DNA was purified using phenol-chloroform followed by ethanol precipitation. Biotinylated but unligated ends were removed using T4 DNA polymerase by incubating at 12 C for 15 minutes. The material was fragmented to 300-600 bases by sonication. The fragment ends were repaired and A-tailed. Then the biotinylated fragments were bound to streptavidin beads and unbound fragments were washed away. Sequencing adapters were then ligated to the fragments bound to beads. The material was amplified 6-9 cycles while bound to beads to obtain sufficient amount for sequence capture. Original biotinylated material was removed, supernatant was hybridized to sequence capture probe set according to manufacturer's instructions (Roche Nimblegen Inc.). Hybridized material was washed according to manufacturer's instructions and amplified with PCR for 3-6 cycles. The following DNA libraries were sequenced 100 bp from both ends (paired-end sequencing) on a Hi Seq 2000 (Illumina Inc.).

Mapping of Sequence Data.

Paired-end sequences were aligned to the mouse genome (build mm9) using Bowtieversion 0.12.7 with option −m 1, in single-end mode for the two ends separately, and with iterative trimming from the 3' end for unaligned reads, 5 bases at a time, until they aligned. Multi-mapping reads were discarded. Paired-end mapping is not suitable for HiCap libraries as the 100 base pairs on either end often contain the ligation point so that a paired-end mapper would soft trim that sequence end so to effectively remove the pairing information. We therefore used custom scripts to pair the independently mapped sequence ends and we indexed each sequence pair to their corresponding MboI restriction fragment.

Sequence Capture Probes.

We designed sequence capture probes against mouse promoters that were compiled from multiple sources. RefSeq and Ensembl annotations were used to together with transcription start sites from DBTSS (from 25 May 2010) and MPromDb (from 28 May 2010). DBTSS is based on full-length mRNAs, and mostly corresponds to RefSeq and Ensembl. MPromDb is based on RNA PolII and H3K4me3 ChIP-seq data for different cell types including ES cells. From annotated transcript start sites, we searched for the closest restriction cut sites (GATC) on each side, and chose the 150 last by before the cut site as the captured regions. When restriction sites were <300 bp apart we chose the whole region between them. From these regions, Nimblegen designed the actual probe sequences. We also selected exonic and intergenic control regions from which were included in the same probe selection pipeline.

Calling of Interactions.

We called significant interactions for all promoter containing restriction fragments. To this end, aligned pairs of which at least one mate mapping on a promoter were selected. Promoter regions were defined as 1000 bases downstream and 3000 bases upstream of transcription start site. The extension allowed mappings involving the directly surrounding fragment of the promoter-anchored fragment to be incorporated into analyses, as restriction cut efficiency was only 71%. We collected all paired sequences with one end originating from a promoter region and the other end at least 1000 bp away from the promoter region. Next we counted the occurrence of interactions to all MboI restriction fragments in the genome from each captured promoter region. Read pairs with the exact same mapping positions were discarded (to remove any potential effect from PCR duplicates). The same procedure was applied to the negative control regions to obtain read pairs for interactions that were later used as background interaction probabilities. We binned all negative control interactions distances (bin size of 1 kb) and calculated the average and standard deviation of the number of interactions found per fragment for negative control regions (discarding fragments with zero interactions from the calculations). These background probabilities of interactions were then used to assess whether each promoter-anchored interaction was significant in each biological replicate independently, using a Z-test. We adjusted the P-values, to account for the multiple tests performed, using the Benjamini-Hochberg procedure and we required a significant interaction to have adjusted P-values below 0.2 in both biological replicates, resulting in an effective adjusted P-value threshold of 0.04 since interactions were required to be present in both biological replicates. Additionally, we required at least 4 supporting read pairs in each biological replicate and for high-confidence interactions we required 14 read pairs per replicate. Promoter-promoter interactions were called similarly, but requiring that both ends of the paired reads aligned within the annotated promoter regions. We also mined the raw read pairs for interactions involving only enhancers. For this purpose we collected all distal regions from significant promoter-distal interactions and performed similar analyses for read pairs with both ends originating from a HiCap mapped distal region. Enhancer regions were not extended, so their resolution corresponded to restriction fragments.

Analyses of Overlap with Enhancer ChIP-Seq Data.

We downloaded enhancer regions inferred in different ChIP-seq experiments carried out in mESC and K562 cells. We sorted the mapped regions in each experiment to only analyze the top 5,000 mapped regions from each experiment, in order to control for different signals and background levels in the different experiments. For Mediator data, we downloaded raw reads for Med1 (SRX022694 and SRX022695) and Med12 (SRX022692 and SRX022693) and aligned to the mouse genome mm9. We performed peak calling using SISSRs version 1.4, concatenated and sorted the peaks. ChIP-seq mapped regions were extended to 1,000 bp if they were shorter (relevant only for Mediator bound regions). For analyses comparing HiCap and ChIA-PET overlap with known enhancers, we computed the observed to the expected overlap. The observed overlap was simply computed as the fraction of HiCap or ChIA-PET interactions that overlapped (with a least 1 nt) with enhancer mapped regions. To compute the expected overlap we randomly sampled regions close to annotated TSS sites, using the actual distance distribution of HiCap interactions. Similarly, expected ChIA-PET overlaps used the actual distance distribution in ChIA-PET interactions. We found this procedure to better control for the non-random locations of genes and enhancers in the genome, whereas the computation of expected overlap based on a fully random model (the fraction of genomic fragments overlapping with known enhancer) rendered all tests significant.

Comparisons of Enhancer Overlap Between HiCap and ChIA-PET Interactions.

We downloaded promoter-enhancer interactions mapped with ChIA-PET in K562 cells and mESC. We analyzed 33,682 interactions reported in K562 for which anchor information in published interaction table indicated a promoter-enhancer interaction. For mESC interactions that lacked such information, we derived promoter-enhancer interactions through comparisons of the two paired fragments with transcription start sites. We required that only one of the two fragments were within ±2.5 kb of any transcription start sites (RefSeq annotations, 18 Mar. 2014), for which the other fragment was determined to be distal. This procedure identified 7,738 such interactions and the equal amount of high-confidence HiCap interactions was selected for comparison. In comparisons to ChIA-PET data from K562 or mESC, we sorted HiCap interactions according to their p-values and selected the top 33,682 (for K562 comparison) or 7,738 (for mESC comparison) to have equal numbers of HiCap and ChIA-PET interactions for analyses. ChIP-seq peaks for H3K27Ac, H3K4me1, p300, smc3 (cohesin) and CTCF for K562 cells were retrieved from GEO database with the following sample IDs: GSM733656, GSM733658, GSM733692, GSM1003583, GSM935310 and GSM733719 respectively. Also, the corresponding ChIP-seq peaks for mESC were retrieved from GEO database with sample IDs: GSM1000099, GSM1000089, GSM1000121, GSM918750, GSM560343 and GSM918748 respectively. All ChIP-seq peaks were sorted according to their signal (signalValue, ENCODE broadPeak) and top 5,000 regions were used for comparison, in order to control for different signals and background levels in the different experiments. We overlapped ChIA-PET and HiCap enhancers to related ChIP-seq peaks and calculated observed values for each comparison. We computed background distribution by randomly sampling regions close to annotated RefSeq TSS sites, using the actual promoter-enhancer distance distribution from HiCap or ChIA-PET experiment. Control sequences were compared to ChIP-seq peaks to compute expected overlaps. In order to allow for varying expected overlaps (since the length distributions of interactions differ between HiCap and ChIA-PET experiment), we assessed the methods performance by computing the observed minus expected overlap to each ChIP-seq data set.

Comparison of Raw Read Percentages Mapping to Promoters and Enhancer Data in HiCap, Hi-C and ChIA-PET Data.

We used the same number of RefSeq promoter regions (25,267) from mouse assembly mm9 for mESC analyses (for Hi-C and HiCap analyses) and from human assembly hg19 for K562 analyses of ChIA-PET data. Promoter regions were defined as the 1 kb upstream region of annotated TSS. Enhancer locations were based on two representative ChIP-seq experiments on Cohesin (Smc3) and H3K27Ac. We mapped 10 million random raw reads from HiCap, Hi-C and ChIA-PET experiments and reported the fraction unique aligning to the promoter and enhancer sets. P-values were computed using the Chi-square test on the number of aligned reads versus the total number of reads for pair-wise comparisons between methods.

Expression Level Analyses in mESC and K562 Cells.

We prepared RNA-seq library for mESC using Illumina mRNA-seq protocol. The library was sequenced with an Illumina GAIIx at 50 bp read length in single-end mode (Fasteris). Reads were aligned to mouse genome (mm9 assembly) and a comprehensive collection of splice junctions using bowtie (version 0.12.7). We downloaded RNA-seq data from human K562 cells from Sequence read archive (SRX113647) and mapped the sequence reads towards human genome (hg19) using STAR. Expression levels were estimated as reads per kilobase of gene model and million uniquely mapped reads (RPKMs) using Rpkmforgenes, where only uniquely mappable positions were included in the gene model length. Mappability was determined using MULTo and gene models were based on RefSeq annotation downloaded from the UCSC genome browser on 31 Jul. 2011.

Functional Test on HiCap Interactions.

Figure 14:
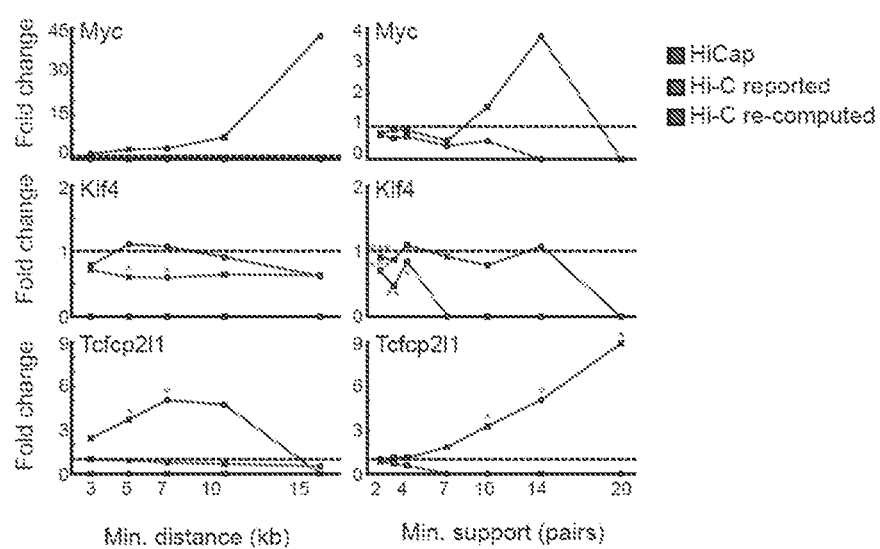
FIG. 14 shows a validation test.

To assess the power of HiCap interactions to predict differentially expressed genes after transcription factor perturbations we constructed the following test. Transcription factor binding data was downloaded from Chen et al., and expression data after transcription factor over-expression. For each transcription factor present in both datasets, we listed the closest gene to each midpoint of the binding region. We identified HiCap interactions connecting promoters to the restriction fragment containing the binding site midpoint and listed the genes of those promoters. For FIG. 5b, we compared the closest gene of peaks without HiCap interactions to the closest genes that also had a HiCap interaction. For FIG. 5d, we compared non-closest genes with HiCap support to the set of closest genes (irrespective of HiCap interactions). This procedure was performed also on Hi-C interactions (both published interactions and those inferred using our interaction calling pipeline). We compared the fraction upregulated genes present within the gene sets and reported the differences as Fold Changes. To explain the test in detail for FIG. 5c-d and FIG. 14, we computed the number of closest genes, Nc, and the number of HiCap-connected genes, Nh. From the expression data we identified differentially expressed genes after each transcription factor perturbation independently (FDR<=0.05 and fold change >1.5). Next, we computed the number of unique genes that were differentially expressed and also present in either the set of closest genes (Uc) or HiCap inferred (non-closest) genes (Uh). We summarized the enrichments as fold changes [Uh/Nh]/[Uc/Nc] and calculated a P-value using chi-square test with Uh and Uc as observed and Nh/Nc as their expected ratio. For the compound test including all transcription factors, we summed all values of Nc Nh, Uc, Uh and performed the same tests.

Analyses of Enhancer RNA Expression.

We re-analyzed mapped RNA-seq data present in Gene Expression Omnibus (GSM935897 and GSM935898) to determine expression levels for HiCap inferred putative enhancers. In parallel, reads from GSM854404 were mapped to putative ChIA-PET enhancers using Star. Unique alignments were used to calculate RPKM expression levels for each HiCap or ChIA-PET inferred region. P-values were computed using Chi-square test based on the fraction of putative enhancers from HiCap and ChIA-PET with expression above either 0.1 or 1.0 RPKM.

Interaction Motifs.

We mined the HiCap interactions between promoters and enhancers to enumerate the occurrences of motifs (FIG. 6a-j). To calculate P-values, we grouped interactions by distance (1000-1999, 2000-3999, 4000-7999 etc up to 64000-127999) and by the sum of the degrees of the promoter nodes (2, 3, 4 etc up to 20). We then performed a one-tailed Wilcoxon rank sum test for each group (for 0 vs 1 or 1 vs 2+ enhancers), and combined the P-values by Stouffer's z-score method, to compute two-tailed P-values. The P-values were also significant ($P<1e^{-300}$) without this consideration for distance and network degree.

Gene Ontology Analyses of Interconnected Gene Pairs.

We tested if gene pairs connected through promoter-promoter, promoter-enhancer-promoter interactions more often shared annotated gene function. To this end, we used the gene ontology service DAVID[6]. First we calculated for each gene ontology term how many gene-pairs were connected through one or more HiCap interactions in the patterns outlined in FIG. 6m for genes within that gene ontology term. Then we randomized (n=1000) all HiCap interactions among all promoters and enhancers and repeated the same analyses above. We computed p-values as the number of randomizations with at least as many pairs as the non-randomized, or one less (to account for selecting terms with at least one real pair to them). Due to the 1000 randomizations, the minimum possible P-value was 0.001. P-values were then adjusted to False Discovery Rates using the Benjamini-Hochberg method.

Example 3

In another exemplifying case the HiCap method was applied as:

1. Sequence probes targeting promoters of relevant organism was designed
2. Around 5 million cells (30 ug DNA) are crosslinked using 1% formaldehyde for 10 minutes at room temperature. Cells are lysed and nuclei is collected.
3. The nuclei pellet is resuspended in 240 ml of 1.2× restriction enzyme buffer and 3.6 ul 20% SDS (final concentration is 0.3%). The pellet is then incubated for one hour at 37 C by shaking at 950 rpm.
4. Then 27 ul of 20% Triton-X solution (final volume 2%) is added to the pellet and incubated for an hour at 37 C shaking at 950 rpm.
5. 30 ul of FastDigest MboI enzyme (1 U/1 ug of DNA) is added to the pellet and incubated for 4 hours at 37 C shaking at 950 rpm.
6. The enzyme is heat-inactivated by incubation at 65 C for 15 minutes.
7. 156.8 ul of 1× restriction enzyme buffer is added to the digested sample.
7. 1.5 ul of 10 mM dCTP, dGTP and dTTP and 37.5 ul of 0.4 mM of biotin-dATP is added to the digested sample. Then 1.2 ul of Klenow Fragment (10 U/ul,) is added and incubated for 10 minutes at 37 C.
8. 10 ul of 0.5 M EDTA is added to inactivate the enzyme and sample is incubated at 75 C for 10 minutes.
9. 9 ml of 1×T4 DNA Ligase ligation buffer is prepared and supplemented with 90 ul of 100 mM ATP. 8090 ul of supplemented 1× ligase buffer is added to the sample (final DNA concentration should be around 3.5 ng/ul). 50 unit of T4 DNA ligase is added to the sample and incubated for 4 hours at 16 C and then 1 hour at room temperature.
10. 25 ul of Proteinase K (20 mg/ml) is added to the sample and incubated at 65 C for 12 hours.
11. A standard phenol-chloroform purification is applied to the sample. An equivolume Phenol Chloroform:IsoamylAlcohol (25:24:1) is added to the sample, mixed well and centrifuged at 3000 rpm for 10 minutes. The aqueous layer is transferred to a new tube and 2.5 volume 100% Ethanol and 0.1 volume 3 M sodium acetate at pH 5.2 is added, mixed well and incubated for one hour at −20 C.
11. Centrifuge the sample at 13,000 rpm for 30 minutes and carefully discard the supernatant without disturbing the pellet.
12. Wash the pellet with 500 ul 70% Ethanol by centrifuging at 13,000 rpm for 5 minutes. Air-dry the pellet for 10 minutes at room temperature and add 100 ul distilled water. The sample is ready for library preparation.
13. Remove biotin from unligated fragments using T4 DNA polymerase following the protocol below:

| | |
|---|---|
| distilled water | 27.0 |
| 5X Buffer (Fermentas) | 20.0 |
| 10 mM dATP | 1.0 |
| 10 mM dGTP | 1.0 |
| DNA (max 5 ug per rxn) | 50.0 |
| T4 DNA Polymerase (3 U/ul) (Fermentas) | 1.0 |
| Total Volume | 100.0 |

Incubate the reaction at 12 C for 15 minutes in a thermocycler. Stop the reactions by adding 2 ul of 0.5 M EDTA and purify the DNA using phenol:chloroform:isoamylAlcohol, followed by ethanol precipitation and resuspend the pellet 100 ul distilled water.
14. Shear the DNA using Covaris sonicator to 250-500 bases using the following setting: Duty cycle: 10%, Intensity:5, cycles per burst:200, time:50×3 seconds, 150 seconds total time. The volume of the sample is 120 ul and each tube should contain maximum of 3 ug DNA.

15. Paired-end DNA sequencing library preparation will be performed by Illumina TruSEQ library preparation kit according to the manufacturer's protocol and described in the following steps "Eight parallel library preparation reactions should produce enough material for sequence capture."

16. 60 ul of sheared DNA (total DNA concentration must not exceed 1 ug) is mixed with 40 ul of End-repair kit from the Illumina library kit and incubated at 30 C for 30 minutes.

17. DNA is then purified using 1.6:1 bead:DNA ratio using Ampure XP beads according to library kit instructions and DNA is eluted in 17.5 ul of resuspension buffer.

18. 12.5 ul of A-tailing buffer is added to the eluted DNA and incubated at 37 C for 30 minutes.

19. In this step, biotinylated fragments will be pulled down using streptavidin magnetic beads. Low-bind tubes should be used from this step onwards. First, prepare the no-tween buffer (NTB) containing 100 mM 1 M Tris-HCl pH 8.0, 2 M NaCl and 1 M EDTA. For bead-washing, prepare the tween wash buffer by diluting the NTB two fold and adding 1 ul tween-20. Then 100 ul of streptavidin beads are prepared by washing them twice with 400 ul of tween wash buffer. Washing the beads for the following steps in the protocol are performed as: add the wash buffer to the beads, mix well and incubate at room temperature by rotating for 3 minutes. Place the beads onto a magnet, wait for one minute and discard the supernatant.

16. Resuspend the washed beads in 400 ul NTB.

17. Combine all the DNA in one tube and bring the volume to 300 ul by adding distilled water and combine it with 300 ul of washed beads. Rotate the beads for 15 minutes at room temperature.

18. Reclaim the beads with a magnet and discard the supernatant. Wash the beads with 400 ul two-fold diluted NTB and resuspend them in 30 ul resuspension buffer.

19. Add 2.5 ul of DNA ligase mix, 2.5 ul resuspension buffer and 2.5 ul adapter index and incubate for 10 minutes at 30 C and add 5 ul of stop ligase mix.

20. Clean-up the DNA using Ampure XP beads with 1:1 bead/DNA ratio according to library kit instructions.

21. Perform a 9 cycle standard Illumina PCR according to library kit instructions and ensure that there is at least 1 ug of adaptor-ligated DNA.

22. Original biotinylated fragments are removed by binding the PCR-amplified sample to 30 ul of streptavidin magnetic beads. Beads are incubated at room temperature for 5 minutes and supernatant is collected to a new tube without disturbing the beads.

23. 1 ug of adapter-ligated DNA is hybridised to sequence capture probes according to manufacturer's instructions (Roche Nimblegen Inc). After the hybridisation, probes are washed according to manufacturer's instructions and amplified with PCR 3-5 cycles (Roche Nimblegen Inc). The amplified material is then sequenced in paired-end wise fashion using Illumina HiSeq platform. It is advisable to perform a shallow sequencing first to check if the sequence capture worked before sequencing the sample in depth.

24. Further analysis is performed as described previously.

The invention claimed is:

1. A method comprising:
   i) providing a cross-linked genomic DNA, wherein the DNA is conserved so that the DNA is intact, wherein the DNA comprises a first and a second set of regions;
   ii) fragmenting the cross-linked genomic DNA creating a plurality of cross-linked fragments;
   iii) adding a labelled junction marker and ligating the cross-linked fragments and the marker under conditions such that the marker is ligated to the fragments, thus creating junctions, which junctions are the site of ligation between fragments that are cross-linked, which fragments reside close to each other in the three-dimensional space in a nucleus;
   iv) purifying the fragments containing a marker ligated at the junction;
   v) adding labelled capture probes, which labelled capture probes hybridize to regulatory regions of the cross-linked genomic DNA, and selectively purifying fragments that hybridize to the labelled capture probes; and
   vi) analysing the fragments containing a marker ligated to the junction and which hydridize to the labelled capture probe to determine the identity of the fragments.

2. The method according to claim 1, wherein the fragmentation is created by restriction enzymes.

3. The method according to claim 1, wherein the first and the second set of regions are ligated to each other.

4. The method according to claim 1, wherein the labelled junction marker is labelled by biotin.

5. The method according to claim 1, wherein the first set of regions are promoter regions and the second set of regions comprises a regulatory sequences, being located close or distantly from each other in the DNA or on the same or different chromosomes.

6. The method according to claim 5, wherein said second set of regions comprises enhancer sequences.

7. The method according to claim 5, wherein the regulatory sequences are enhancers, silencers, or insulators.

8. The method according to claim 1, wherein the first region comprises a promoter or regulatory element.

9. The method according to claim 1, wherein the regulatory regions are promotor sequences.

10. A kit, comprising:
    i) an enzyme that will remove biotinylated nucleotides from unligated fragment ends;
    ii) a set of enzymes to prepare sequencing libraries for high-throughput sequencing;
    iii) a labeled junction marker;
    iv) streptavidin beads to select for biotinylated fragments; and
    v) a labeled set of sequence capture probes to capture only fragments complementary to regions of interests, which labelled capture probes hybridize to regulatory regions of a cross-linked genomic DNA.

11. The kit according to claim 10, wherein the labelled junction marker and the set of labeled capture probes are biotin labelled.

* * * * *